(12) United States Patent
Bernstein

(10) Patent No.: US 9,238,017 B2
(45) Date of Patent: Jan. 19, 2016

(54) COMPOSITIONS WITH REDUCED HEPATOTOXICITY

(75) Inventor: Joel E. Bernstein, Deerfield, IL (US)

(73) Assignee: Winston Laboratories, Inc., Vernon Hills, IL (US)

( * ) Notice: Subject to any disclaimer, the term of this patent is extended or adjusted under 35 U.S.C. 154(b) by 178 days.

(21) Appl. No.: 13/197,581

(22) Filed: Aug. 3, 2011

(65) Prior Publication Data

US 2011/0288099 A1 Nov. 24, 2011

Related U.S. Application Data

(62) Division of application No. 10/813,760, filed on Mar. 31, 2004, now abandoned.

(51) Int. Cl.
| | |
|---|---|
| *A61K 31/198* | (2006.01) |
| *A61K 31/167* | (2006.01) |
| *A61K 47/18* | (2006.01) |
| *A61K 9/00* | (2006.01) |

(52) U.S. Cl.
CPC ............. *A61K 31/198* (2013.01); *A61K 9/0019* (2013.01); *A61K 31/167* (2013.01); *A61K 47/18* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 3,983,250 | A | 9/1976 | Abdallah et al. |
| 4,181,719 | A | 1/1980 | Margetts et al. |
| 4,314,989 | A | 2/1982 | Rosen |
| 4,401,657 | A | 8/1983 | Kashiwabara et al. |
| 4,526,788 | A | 7/1985 | Murdock et al. |
| 4,581,348 | A | 4/1986 | Schawartz et al. |
| 4,656,159 | A | 4/1987 | McPherson et al. |
| 4,837,239 | A | 6/1989 | Benjamin et al. |
| 5,059,592 | A | 10/1991 | Yokota et al. |
| 5,284,861 | A | 2/1994 | Lobisch et al. |
| 5,474,757 | A | 12/1995 | Yang |
| 5,478,815 | A | 12/1995 | Ogata et al. |
| 5,597,585 | A | 1/1997 | Williams et al. |
| 5,804,567 | A | 9/1998 | Cheng et al. |
| 5,994,410 | A | 11/1999 | Chiang et al. |
| 6,048,846 | A | 4/2000 | Cochran |
| 6,465,511 | B1 | 10/2002 | Kazmierski et al. |
| 6,468,967 | B1 | 10/2002 | Oelson et al. |
| 6,673,831 | B1 | 1/2004 | Tobert |
| 6,733,797 | B1 | 5/2004 | Summers |
| 6,881,401 | B1 | 4/2005 | Yu et al. |
| 7,371,388 | B1 | 5/2008 | Ruben et al. |
| 7,557,142 | B2 | 7/2009 | Campbell |
| 2009/0124606 | A1 | 5/2009 | Gacsalyi et al. |

FOREIGN PATENT DOCUMENTS

EP 0285343 10/1988

OTHER PUBLICATIONS

Andrade et al., "Assessment of Drug-Induced Hepatotoxicity in Clinical Practice: A Challenge for Gastroenterologists," *World J. Gastroenterol.*, vol. 21:13(3), pp. 329-340 (2007).
Anjum et al., "Sublethal effects of hexavalent chromium on the body rowth rate and liver functions enzymes and phenobarbiton-pretreaed and promethazine-pretreated rabbits," *J. Environ. Pathol. Toxicol. Oncol.*, Abstract, vol. 16:1, pp. 51-59 (1997).
Azari et al., "Effects of Intraperitoneal Injection of Rofecoxib in a mouse model of ALS," abstract, *EP Jrnl. of Neurol.*, vol. 12:5, pp. 357-364 (2005).
DeNoon, "New Warning Labels for Acetaminophen," *WebMD Health, WebMD Medical News Archive* (2002).
"Equivalent Surface Area Dosage Conversion Factors," Guidance Posted Aug. 2007.
"FDA Panel Wants Stronger Acetaminophen Warnings," *SCRIP*, p. 2784 (2000).
Hoekstra et al., "Factors associated with toxicity, final dose, and efficacy of methotrexate in patients with rheumatoid arthritis," *Annals. of Rheumatic Diseases*, British Medical Association, London., 62 (5) 423-426 (2003).
"Intraperitoneal Injection," www.en.wikipedia.org/wiki/intraperitoneal, 2008.
Kroger et al., "Nicotinamide and Methionine Reduce the Liver Toxic Effect of Methotrexate," *General Pharmacology*, vol. 33, pp. 203-206 (1999).
Kroger et al., "Protection from acetaminophen-induced liver damage by the synergistic action of low doses of the poly (ADP-ribose) polymerase-inhibitor nicotinamide and the antioxidant N-acetylcyteine or the amino acid L-methionine," *General Pharmacology*, vol. 28:2, pp. 257-263 (1997).
Laborda et al., "Nephrotoxic and hepatotoixic effects of chromium compounds in rats," *Bull. Environ. Contain. Toxicol.*, Abstract, vol. 36:3, pp. 332-336 (1986).
Lee, *N. England J. Med.*, vol. 394:5, pp. 474-485 (2003).
Legon'kova et al., "The effect of nicotinamide, methionine and alpha-tocopherol on the liver conjugating and mono-oxygenase systems and on lipid peroxidation in hepatosis-hepatitis in rats," *Eksp Klin Farmakol*, Abstract, vol. 60:2, pp. 68-71 (1997).
Martindale, The Complete Drug Reference, 33nd Edition, Pharmaceutical Press, Chelators Antidotes and Antagonists, p. 1012 (2002).
Milano et al., *Antimicrobial Agents and Chemotherapy*, pp. 117-121 (1997).
Stolberg, "Warnings Sought for Popular Painkiller," *New York Times* (2002).
Ulbricht et al., "An evidence-based systematic review of herb and supplement interactions by the natural standard research collaboration," *Expert Opinion*, vol. 5:5, pp. 719-728 (2006).
Vale et al., "Paracetamol (Acetaminophen) Poisoning," *The Lancet*, vol. 346, pp. 547-552 (1995).
Willett et al., "Workshop Overview: Hepatotoxicity Assessment for Botanical Dietary Supplements," *Society of Toxicology*, pp. 1-16 (2004).
Wright et al., "Deaths from Low Dose Paracetamol Poisoning," *British Medical Journal* (England), vol. 317, p. 1656 (1998).

*Primary Examiner* — L. R. Draper
(74) *Attorney, Agent, or Firm* — Barnes & Thornburg LLP; Alice O. Martin

(57) ABSTRACT

Pharmaceutical compositions of hepatotoxic compounds are provided in which the hepatotoxicity of the compounds is mitigated by including quantities of nicotinamide and methionine in the composition. Folic acid also can be included to further mitigate the hepatotoxic effects. The hepatotoxic compounds can include acetaminophen, methotrexate, atorvastatin, simvastatin, niacin, flucanozole, divalproex sodium, and valproic acid.

7 Claims, No Drawings

COMPOSITIONS WITH REDUCED HEPATOTOXICITY

CROSS-REFERENCE TO RELATED PATENT APPLICATIONS

This patent application is a Divisional of copending U.S. patent application Ser. No. 10/813,760, filed Mar. 31, 2004, the contents of which are incorporated herein by reference in their entirety.

FIELD OF THE INVENTION

This invention relates to compositions of pharmaceutical compounds having hepatotoxicity, in which compositions the hepatotoxicity is mitigated. More particularly, this invention relates to compositions of hepatotoxic compounds such as acetaminophen, methotrexate, statin drugs, niacin, divalproex sodium, valproic acid or fluconazole, each of which is known to have hepatotoxic properties, in which compositions the hepatotoxicity of the compound is mitigated.

Acetaminophen is the active metabolite of phenacetin, a drug whose use extends back to the 1880's. Although acetaminophen was first used as an analgesic and antipyretic in 1893, it did not achieve widespread use until after 1949. For many years, acetaminophen was used as a second-line choice to aspirin as an analgesic/antipyretic, but the elucidation of the relationship between aspirin use and Reye's Syndrome and the recognition of aspirin's propensity to produce gastrointestinal bleeding vaulted acetaminophen into its current day position as the analgesic/antipyretic of first choice in both children and adults. While acetaminophen is usually well tolerated, its use can be accompanied by a very serious adverse effect—potentially fatal hepatic necrosis. Hepatic necrosis with acetaminophen is largely confined to two groups of patients: 1. Patients who ingest acute overdoses or who chronically utilize high dosage regimens of acetaminophen. 2. Ingestion of acetaminophen by alcoholics or in combination with alcohol ingestion. It has been reported that more than 26,000 patients per year are hospitalized in the U.S. for acetaminophen induced hepatic necroses, and of these, more than 400 die each year. Many of these overdoses are the result of suicide attempts, but reports indicate that more than 2,000 hospitalizations and 100 deaths a year were attributable to non-intentional acetaminophen overdoses. In fact, an Advisory Panel of the U.S. Food and Drug Administration has recommended that new warning language be added to the label of acetaminophen containing products concerning the danger of hepatic necroses.

Methotrexate, an inhibitor of cell metabolism, has been utilized for several decades as a therapeutic agent widely used in several different diseases including rheumatoid arthritis and psoriasis. While methotrexate administration is associated with various other side effects, severe and sometimes fatal liver toxicity is a significant limiting factor in its therapeutic usefulness. Atorvastatin, simvastatin and other cholesterol reducing agents of the "statin" family are the most widely used pharmaceuticals in the world. In spite of their widespread use, liver toxicity is a significant problem, and patients with a history of old or active hepatitis must avoid these drugs even if they could benefit from their cholesterol lowering actions. Niacin (also known as nicotinic acid or vitamin $B_3$), another agent frequently employed as a cholesterol lowering agent, is also associated with a high incidence of liver toxicity. Fluconazole, a potent antifungal agent, and divalproex sodium and valproic acid, widely used antiepileptics are three other agents whose clinical use is limited by their hepatotoxicity.

The concerns about the hepatic toxicity of acetaminophen, methotrexate, the "statin" cholesterol lowering agents, niacin, fluconazole, divalproex sodium and valproic acid, prompted me to search for a substitute or a mixture of substances that in combination with any of these drugs would substantially reduce the risk of hepatic toxicity without adversely affecting the therapeutic benefits conferred by these drugs. In reviewing the scientific literature, I learned that nicotinamide (also known as niacinamide), which is the amide of vitamin $B_3$ (niacin), and methionine, an essential amino acid which is a DL racemic mixture of D & L methionine, have been used in very high dosages to prevent liver damage from acetaminophen or methotrexate. These drugs have been administered as single large doses or multiple large doses over a short (usually 24 hr) period. Published dosages of methionine for such usage range from about 2.5 gm to over 21 gm administered as a single dose for over 24 hours. Wright, B., Crowe, M., British Medical Journal (England), vol. 317, Dec. 12, 1998, p. 1656; Vale, J. A., Proudfoot, A. T., The Lancet, 1995, vol. 346, pp. 547-52. Similarly, doses of nicotinamide utilized for a similar purpose have ranged from about 2 gm to 7 gm per 24 hours. Kroger, H., et al., General Pharmacology 33 (1999) 203-206.

I have discovered, surprisingly, that nicotinamide and methionine can be administered in combination with hepatotoxic pharmaceutical compounds such as acetaminophen, methotrexate, a "statin" cholesterol lowering agent, fluconazole, divalproex sodium or valproic acid, in substantially lower doses than disclosed in the prior art, and when administered as such, can provide a substantive protective effect against the hepatotoxicity of these agents without negatively affecting their beneficial therapeutic activity. I have furthermore discovered that by adding a modest amount of folic acid to the nicotinamide and methionine mixture, in combination with hepatotoxic pharmaceutical compounds such as acetaminophen, methotrexate, atorvastatin, simvastatin, niacin, fluconazole, divalproex sodium, valproic acid, and related drugs, I can achieve a therapeutic product which provides the therapeutic benefits of each of these agents with almost no potential for liver toxicity.

It is thus the object of the invention to provide pharmaceutically acceptable compositions of hepatotoxic drugs such as acetaminophen, methotrexate, the "statins," niacin, fluconazole, divalproex sodium, valproic acid, and related drugs, which compositions provide the therapeutic benefits of the active drug with markedly reduced potential for serious hepatotoxicity.

DETAILED DESCRIPTION OF THE PREFERRED EMBODIMENTS

In accordance with the invention, compounds having known hepatotoxic properties are formulated into compositions in which the hepatotoxic properties are mitigated. The compositions can include a standard dose of the hepatotoxic compound, together with relatively low dosages of nicotinamide and methionine. Low dosages of folic acid also can be added to the compositions to further mitigate the hepatotoxic properties.

Specific embodiments of the invention can be in the form of formulations of acetaminophen together with mixtures of low dosages of nicotinamide and methionine, or together with low dosages of nicotinamide, methionine and folic acid; or formulations of methotrexate together with mixtures of low dosages of nicotinamide and methionine, or together with low dosages of nicotinamide, methionine and folic acid. These formulations are incorporated into pharmaceutically acceptable vehicles for use in humans and animals. Similarly, formulations of atorvastatin, simvastatin, niacin, fluconazole, divalproex sodium or valproic acid each can be formulated into pharmaceutically acceptable vehicles for use in humans and animals together with mixtures of low dosages of nicotinamide and methionine, or together with low dosages of nicotinamide, methionine and folic acid. Such formulations include those suitable for oral administration such as capsules, tablets, caplets, or liquid solutions or suspensions, as well as sterile solutions or suspensions suitable for intradermal, subcutaneous, intramuscular, intravenous or intrathecal injection.

In each of the foregoing formulations, whether for oral ingestion or for injection, when combined with standard dosages of either acetaminophen (80 mg-1000 mg per single dose form, e.g. single capsule, single tablet, etc.), methotrexate (2.5 mg-250 mg per single dose form), atorvastatin or simvastatin (5 mg-100 mg per single dose form), niacin (250 mg-1000 mg per single dose form), fluconazole (10 mg-250 mg per single dose form), divalproex sodium (100 mg-750 mg per single dose form), and valproic acid (25 mg-500 mg per single dose form), methionine may be present in the amount of about 5 mg to about 500 mg per single dose form, and preferably about 10 mg to 100 mg per single dose form, and nicotinamide may be present in the amount of about 10 mg to 500 mg per single dose form, and preferably about 25 mg to about 200 mg per single dose form. When folic acid is included in the standard dose formulation, folic acid may be present in the amount of about 50 mcg to about 5 mg, and preferably about 500 mcg to 1 mg, per single dose form.

Suitable pharmaceutical vehicles for the combinations of hepatotoxic compounds such as acetaminophen, methotrexate, atorvastatin, simvastatin, niacin, fluconazole, divalproex sodium or valproic acid, with hepatotoxicity mitigators methionine, nicotinamide and folic acid, and methods of preparing such formulations as are within the scope of the invention, will be readily apparent to and understood by those skilled in the art.

The compositions of the instant invention will be more readily comprehended from the following examples:

EXAMPLES

Example 1

Two tablets, comprised of 500 mg acetaminophen, 50 mg methionine, and 25 mg nicotinamide, are administered to patients with painful osteoarthritis four times daily for 12 weeks producing substantial relief of joint pain without evidence of any hepatotoxicity.

Example 2

Capsules are prepared each containing by weight 325 mg acetaminophen, 50 mg methionine, 50 mg nicotinamide, and 500 mcg folic acid. One to two of such capsules are administered to patients with osteoarthritis or fibromyalgia pain four to six times daily for 6 months for relief of joint or soft tissue pain without evidence of damage to the patients' livers.

Example 3

Two caplets each containing 500 mg acetaminophen, 200 mg methionine, and 100 mg nicotinamide are administered four times daily for twelve (12) weeks to patients with osteoarthritis for relief of osteoarthritis pain without evidence of liver damage.

Example 4

Tablets are prepared each containing 2.5 mg methotrexate, 100 mg methionine, 100 mg nicotinamide and 100 mcg folic acid. Two of such tablets are administered to patients with psoriasis of the skin twice daily for 6 months. Such patients demonstrate improvement in their psoriatic lesions without evidence of serious methotrexate-induced liver damage.

Example 5

Tablets containing 250 mg divalproex sodium, 250 mg methionine and 100 mg nicotinamide by weight are administered twice daily to patients with migraine headaches to prevent or diminish the severity of migraine headaches without evidence of serious liver damage.

Example 6

Capsules are prepared each containing by weight 10 mg atorvastatin, 500 mg methionine, 100 mg nicotinamide, and 1.0 mg folic acid and administered to patients once daily. Such patients have lower serum cholesterol and triglycerides without evidence of significant alteration in their liver functions.

Example 7

An oral suspension containing 10 mg/ml fluconazole, 25 mg/ml methionine and 20 mg/ml nicotinamide is administered to children for treatment of oropharyngeal candidiasis at a dosage of 2-12 mg/kg per day for 3 weeks with a substantially lessened risk of liver toxicity than with standard fluconazole suspensions.

What is claimed is:

1. A method of mitigating the hepatotoxicity of a hepatotoxic compound, the method comprising:
    formulating a composition of the hepatotoxic compound by combining a quantity of the hepatotoxic compound with a quantity of nicotinamide, a quantity of methionine, and a quantity of folic acid into a single individual dosage form selected from the group consisting of a capsule, a tablet or an oral solution,
    and further administering the individual dosage form containing the hepatotoxic compound, nicotinamide, folic acid, and methionine to a patient in need of the hepatotoxic compound,
    wherein the hepatotoxic compound is selected from the group consisting of acetaminophen, atorvastatin, simvastatin, niacin, fluconazole, divalproex sodium, and valproic acid.

2. The method of claim 1 wherein said composition is formulated such that for each dose of the hepatotoxic compound in the composition, the nicotinamide is present in the amount of 5-500 mg, and the methionine is present in the amount of 25-500 mg.

3. The method of claim 2 wherein said nicotinamide is present in the amount of 25-200 mg per dose of the hepatotoxic compound.

4. The method of claim 2 wherein said methionine is present in the amount of 10-100 mg per dose of the hepatotoxic compound.

5. The method of claim 1 wherein said folic acid is present in the amount of 50 mcg-5 mg per dose of the hepatotoxic compound.

6. The method of claim 5 wherein said folic acid is present in the amount of 500 mcg-1 mg per dose of the hepatotoxic compound.

7. The method of claim 1, wherein said acetaminophen is present in the amount of 80 mg-1000 mg per dose.

\* \* \* \* \*